United States Patent
Fuchs et al.

[19]

[11] Patent Number: 5,980,538
[45] Date of Patent: Nov. 9, 1999

[54] SURGICAL SUTURING INSTRUMENT

[75] Inventors: Werner Fuchs, Hauptstrasse 41, A-2443 Loretto, Austria; Harald Boszotta, Steinbrunn, Austria

[73] Assignee: Werner Fuchs

[21] Appl. No.: 09/146,700

[22] Filed: Sep. 3, 1998

[30] Foreign Application Priority Data

Sep. 9, 1997 [AT] Austria .................................. 1517/97

[51] Int. Cl.⁶ .................................................. A61B 17/04
[52] U.S. Cl. ........................... 606/145; 606/139; 606/144
[58] Field of Search .................................. 606/139, 144, 606/145, 147

[56] References Cited

U.S. PATENT DOCUMENTS

| | | | |
|---|---|---|---|
| 1,815,725 | 7/1931 | Pilling et al. | 606/145 |
| 1,822,330 | 9/1931 | Ainslie | 606/145 |
| 1,856,721 | 5/1932 | Nagelman | 606/145 |
| 2,577,240 | 12/1951 | Findley | 606/145 |
| 3,842,840 | 10/1974 | Schweizer | 606/145 |
| 4,164,225 | 8/1979 | Johnson et al. | 606/145 |
| 5,454,823 | 10/1995 | Richardson et al. | 606/145 |

FOREIGN PATENT DOCUMENTS 24 47 719  10/1974  Germany .

*Primary Examiner*—Gary Jackson
*Attorney, Agent, or Firm*—Herbert Dubno; Andrew Wilford

[57] ABSTRACT

A surgical suturing instrument has an elongated housing forming a stationary jaw and a movable jaw formed with a holder for a suture filament and pivotal on the housing between a closed position closely juxtaposed with the stationary jaw and an open position spaced therefrom. A first actuating member displaceable in the housing is coupled to the movable jaw for moving it between its positions. A needle is movable in the housing between a position recessed in the housing and an extended position projecting crosswise from the housing to the movable jaw in the open position thereof. A second actuating member displaceable in the housing independently of the first actuating member is coupled to the needle for moving it between its positions.

11 Claims, 2 Drawing Sheets

SURGICAL SUTURING INSTRUMENT

FIELD OF THE INVENTION

The present invention relates to a surgical suturing instrument. More particularly this invention concerns an apparatus for attaching sutures during arthroscopic or laparascopic surgery.

BACKGROUND OF THE INVENTION

In various arthroscopic procedures, for instance reattachment of a rotator-cuff tendon, it is necessary to attach a suture to an internal body part and then to secure this suture to another part. For instance a suture is passed through a detached tendon and is then secured to a hole or anchor in a bone.

To minimize trauma, this surgery is conducted arthroscopically or laparascopically, that is through a small hole in the patients skin. The tool that attaches the suture must therefore be of narrow dimensions so that it can be inserted through the access hole.

A typical device as described in U.S. Pat. No. 5,522,820 of Caspari has a pair of jaws, one of which is movable. A piercing needle with a hook end is fixed to one of the jaws and the other jaw is set up to hold a suture filament so that when the two jaws are moved together the needle pierces the body part between them and the suture is picked up by the hook end of the needle and pulled back through the part as the jaws are again separated In use the jaws are opened and then positioned to opposite sides of the tendon or other body part to be sutured, then they are pressed together so that the needle pierces this part. When the jaws are again opened, the needle pulls out of the hole it has made and draws the suture filament back through it.

The disadvantage of this system is that it is relatively thick, requiring a hole some 12 mm across to fit through In addition when open it is some 18 mm to 20 mm wide, so that it stretches out the body region where it is being employed and cannot be fit into tight locations. Furthermore it is relatively difficult to position it so that it pierces the body part just where desired, especially if, for instance, the part is a retracted tendon.

German patent document 2,447,719 of Schweizer describes another such system that basically operates like a pair of forceps that is closed on the part to be sutures so that it first clamps this part, then automatically pierces it and threads a suture through it. This device is relatively bulky and not suitable for arthroscopic work. Furthermore it must be perfectly positioned before being closed, as once it is closed on the part the needle is automatically advanced.

OBJECTS OF THE INVENTION

It is therefore an object of the present invention to provide an improved surgical suturing instrument.

Another object is the provision of such an improved surgical suturing instrument which overcomes the above-given disadvantages, that is which is narrow enough for use in arthroscopic or laparascopic surgery and which can be accurately positioned even in very tight surroundings

SUMMARY OF THE INVENTION

A surgical suturing instrument has according to the invention an elongated housing forming a stationary jaw and a movable jaw formed with a holder for a suture filament and pivotal on the housing between a closed position closely juxtaposed with the stationary jaw and an open position spaced therefrom. A first actuating member displaceable in the housing is coupled to the movable jaw for moving it between its positions. A needle is movable in the housing between a position recessed in the housing and an extended position projecting crosswise from the housing to the movable jaw in the open position thereof. A second actuating member displaceable in the housing independently of the first actuating member is coupled to the needle for moving it between its positions.

Thus with the system of this invention the jaws can be opened and closed independently of operation of the needle. Thus the tool can be used to grip and position a body part and can even release it to gain a new grip. Once the desired position is attained, the second actuating member is operated to pierce the needle through the part and draw back the suture filament.

The surgical suturing instrument wherein the housing is formed with a longitudinal guide receiving the needle in the recessed position and with an abutment deflecting the needle transversely of the housing on displacement in to the extended position.

According to a further feature of the invention a link has a front end pivoted on a rear end of the needle and a rear end pivoted on the second actuating member. The second actuating member is displaceable solely longitudinally in the housing. In addition the housing is formed with an arcuate guide controlling movement of the front end of the link. This guide is generally S-shaped. In addition the housing is formed with a slot open toward the movable jaw and holding the needle in the recessed position. The guide includes a pin bridging the slot and riding on the needle as it moves between its positions. The movable jaw is formed with a slot into which the needle engaged in its extended position.

The first actuating member according to the invention is a tube coaxially surrounding the second actuating member and the second actuating member has a slot through which the movable jaw extends. A link has a rear end pivoted on the first actuating member and a front end pivoted on the movable jaw. This movable jaw has a forked rear end pivoted on the housing and straddling the second actuating member. For a system that is very compact the housing and first actuating member are coaxial tubes coaxially surrounding the second actuating member.

BRIEF DESCRIPTION OF THE DRAWING

The above and other objects, features, and advantages will become more readily apparent from the following description, reference being made to the accompanying drawing in which:

FIG. 3 are sectional side views of another suturing instrument in accordance with the invention in the closed and open positions.

SPECIFIC DESCRIPTION

Figure 1:
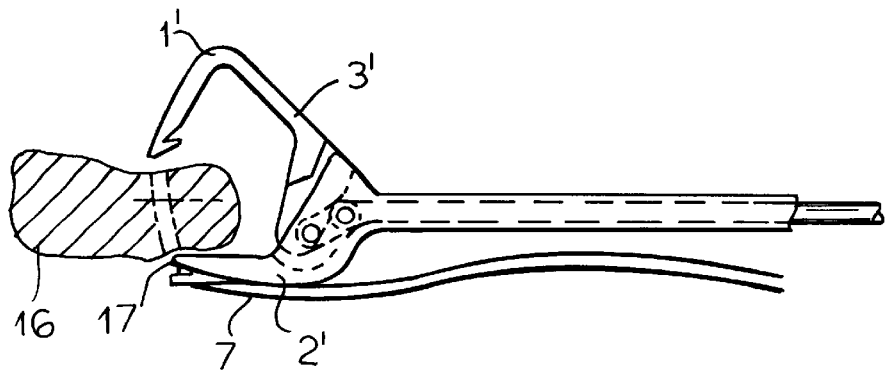
FIG. 1 is a side view of a prior-art suturing instrument.

As seen in FIG. 1 a prior-art suturing device has a needle 1' that forms part of a movable jaw 3' and a fixed jaw 2' that has a seat 17 for a suture filament 7. This device is closed on a tendon 16 to pierce a hole through it, with the hooked end of the needle 1' engaging the suture 7 and pulling it back through the hole when the device is opened. This device must therefore be positioned perfectly at the tendon 16 and then closed so as to grab it, form the hole, pass the suture through it, and release it, these operations all following automatically after one another as the device is closed and opened.

Figure 2:
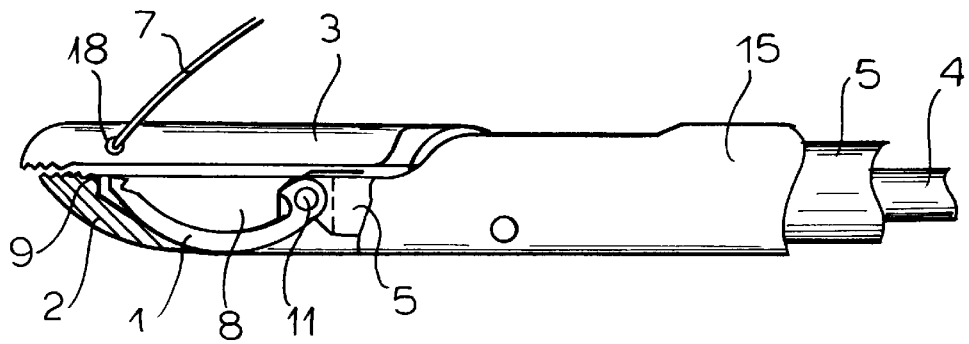
FIGS. 2 and 3 are partly sectional side views showing a suturing apparatus according to the invention in the closed and open positions.
Figure 3:
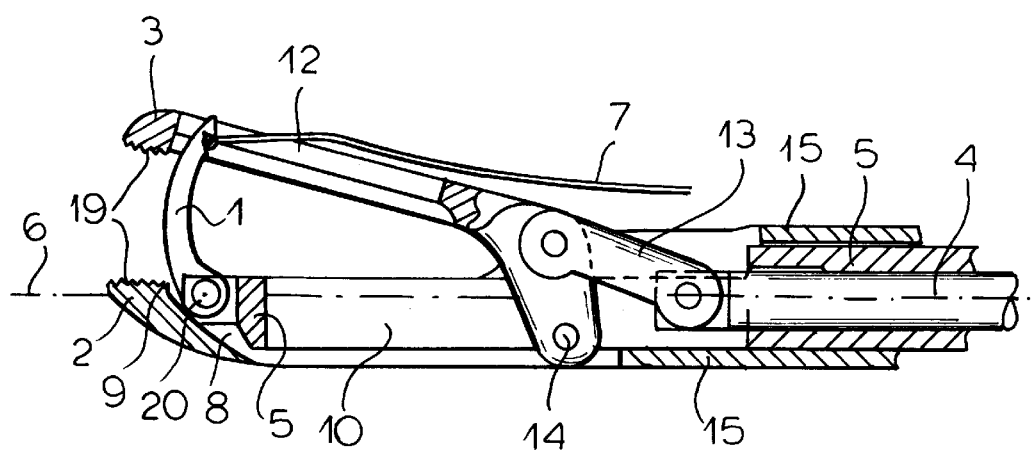

With the system of this invention as shown in FIGS. 2 and 3 it is possible to grab, manipulate, and release a body part and to pierce and suture it only when the operator is satisfied the part has been properly grabbed and/or positioned. Thus with this system the tendon can be pulled, released, and reengaged if necessary to position the tool for suturing in the best location.

To this end the device has a cylindrically tubular housing 15 some 7 mm in diameter and all its parts lie in a longitudinal extension of this housing 15 so it can be inserted through a relatively small access hole. The housing 15 itself has an outer end forming a fixed jaw 2 and an L-shaped pivotal jaw 3 has a forked rear end pivoted at a transverse axis 14 on the housing 15. This jaw 3 is formed with a longitudinally extending slot 12 and with a through-going hole 13 through which the suture filament 7 extends. The tubular housing 15 internally accommodates an axially slidable outer actuating tube or member 5 and, coaxially therein, a axially slidable inner actuating rod or member 4. A link 13 has a rear end pivoted on the outer end of the rod 4 and a front end pivoted at the corner of the L-shaped jaw 3 offset from the axis 14. Thus displacement along an axis 6 of the device of the rod 4 will move the jaw 3 between the closed position of FIG. 2 to the open position of FIG. 3.

Pivotally mounted at 11 on a front end of the member 5 is the rear end of an arcuate needle 1 having a hooked outer end that can engage in the slot 12 at the hole 18. The needle 1 is accommodated in a slot 8 formed in the housing 15 and can engage an axially rearwardly directed abutment 9 formed by the jaw 3. A torque spring 20 around the pivot 11 urges the needle 1 counter-clockwise into a position recessed in the slot 8. The member 5 is formed with a slot 10 through which engages the movable jaw 3 so that the members 4 and 5 can move axially independently of each other. The confronting surfaces of the outer ends of the jaws 2 and 3 are formed with crosswise gripping ridges 19.

With this system it is possible to operate the device as a simple clamp by use of the member 5 to open and close the jaws 2 and 3. Thus the tool can be moved about to engage, pull, and position a tendon to be sutured, and can even be opened and repositioned if necessary. Once it is in the desired position, the rod 4 is pushed to force the needle 1 forward. As the needle 1 advances it is deflected upward through the gripped tendon by the abutment 9 and into the slot 12 where it engages the suture 7. The rod 4 is then retracted to pull the needle 1 back, drawing the hooked suture filament 7 through the hole just formed, and then the member 5 can be retracted to release the sutured tendon.

Figure 4:
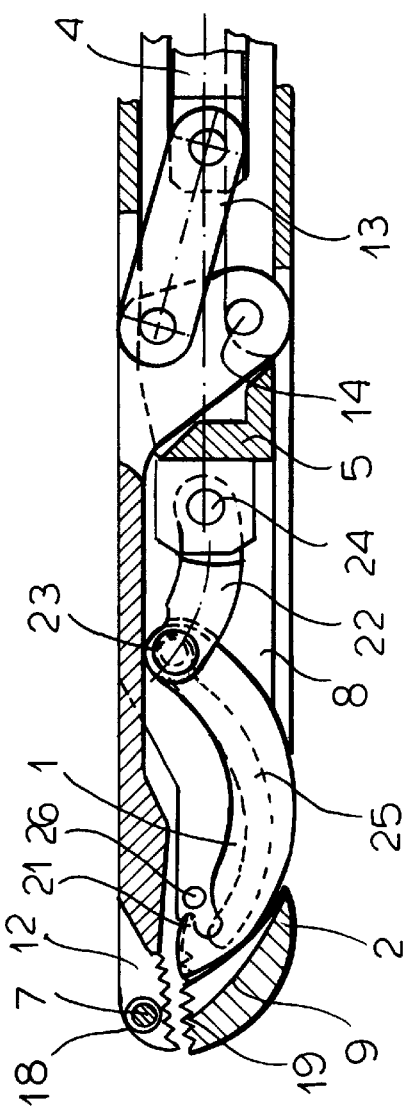
FIGS. 4 and 5 are partly sectional side views of another embodiment of the instrument according to the invention.
Figure 5:
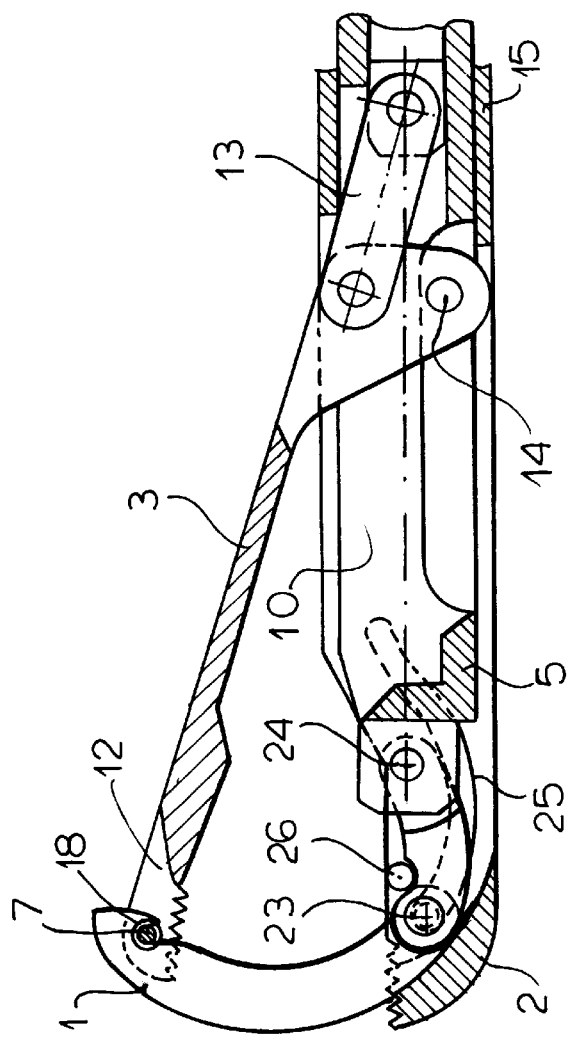

In the arrangement of FIGS. 4 and 5, where reference numerals identical to those of FIGS. 2 and 3 are used for functionally identical structure, the needle 1 has a rear end provided with a crosswise pivot pin 23 pivoted on the front end of an arcuate link 22 whose rear end is pivoted at 24 on the member 5. The front pivot pin 23 is guided in a pair of confronting S-shaped guide grooves 25 formed in the housing 15. A guide pin 26 rides on the upper edge of the needle 1 and even on the link 22 as same are extended forward.

This arrangement works identically to that of FIGS. 2 and 3, except that the needle 1 is guided somewhat more positively and accurately. The device can be used as a simple gripper and manipulator that pierces through a gripped part and threads a suture through it in a separate operation, once everything is in the desired position.

We claim:

1. A surgical suturing instrument comprising:

an elongated housing forming a stationary jaw;

a movable jaw formed with a holder for a suture filament and pivotal on the housing between a closed position closely juxtaposed with the stationary jaw and an open position spaced therefrom;

means including a first actuating member displaceable in the housing and coupled to the movable jaw for moving it between its positions;

a needle movable in the housing between a position recessed in the housing and an extended position projecting crosswise from the housing to the movable jaw in the open position thereof; and means including a second actuating member displaceable in the housing independently of the first actuating member and coupled to the needle for moving it between its positions.

2. The surgical suturing instrument defined in claim 1 wherein the housing is formed with a longitudinal guide receiving the needle in the recessed position and with an abutment deflecting the needle transversely of the housing on displacement in to the extended position.

3. The surgical suturing instrument defined in claim 2, further comprising a link having a front end pivoted on a rear end of the needle and a rear end pivoted on the second actuating member, the second actuating member being displaceable solely longitudinally in the housing.

4. The surgical suturing instrument defined in claim 3 wherein the housing is formed with an arcuate guide controlling movement of the front end of the link.

5. The surgical suturing instrument defined in claim 4 wherein the guide is generally S-shaped.

6. The surgical suturing instrument defined in claim 4 wherein the housing is formed with a slot open toward the movable jaw and holding the needle in the recessed position, the guide including a pin bridging the slot and riding on the needle as it moves between its positions.

7. The surgical suturing instrument defined in claim 1 wherein the movable jaw is formed with a slot into which the needle engaged in its extended position.

8. The surgical suturing instrument defined in claim 1 wherein the first actuating member is a tube coaxially surrounding the second actuating member and the second actuating member has a slot through which the movable jaw extends.

9. The surgical suturing instrument defined in claim 1, further comprising a link having a rear end pivoted on the first actuating member and a front end pivoted on the movable jaw.

10. The surgical suturing instrument defined in claim 1 wherein the movable jaw has a forked rear end pivoted on the housing and straddling the second actuating member.

11. The surgical suturing instrument defined in claim 1 wherein the housing and first actuating member are coaxial tubes coaxially surrounding the second actuating member.

* * * * *